United States Patent [19]

James

[11] 4,032,702
[45] June 28, 1977

[54] PRODUCTION OF SURFACE ACTIVE MATERIAL

[75] Inventor: Kenneth James, Reading, England

[73] Assignee: Tate & Lyle Limited, London, England

[22] Filed: Oct. 15, 1975

[21] Appl. No.: 622,495

[30] Foreign Application Priority Data

Oct. 17, 1974 United Kingdom ............. 45122/74
Apr. 18, 1975 United Kingdom ............. 16222/75

[52] U.S. Cl. ............................. 536/119; 252/89 R; 252/352; 424/361; 426/608; 536/115
[51] Int. Cl.$^2$ ........................................ C07H 13/06
[58] Field of Search ................ 260/234 R; 536/115, 536/119

[56] References Cited

UNITED STATES PATENTS

| 3,251,827 | 5/1966 | Schnell et al. | 260/234 R |
| 3,558,597 | 1/1971 | von Brachel et al. | 260/234 R |
| 3,597,417 | 8/1971 | Myhre | 260/234 R |
| 3,714,144 | 1/1973 | Feuge et al. | 260/234 R |
| 3,748,324 | 7/1973 | Mizutani et al. | 260/234 R |

*Primary Examiner*—Johnnie R. Brown
*Attorney, Agent, or Firm*—Ostrolenk, Faber, Gerb & Soffen

[57] ABSTRACT

A surface active material is prepared by reacting solid particulate sucrose with at least one alkyl ester of a fatty acid in the presence of a basic trans-esterification catalyst, at a temperature from 110° to 140° C, at atmospheric pressure and in the absence of any solvent. The reaction product may be purified by conversion of fatty acids and salts thereof into soaps, extracting the water-insoluble material with a ketone or ester solvent and extracting the residue with an alcohol.

16 Claims, No Drawings

PRODUCTION OF SURFACE ACTIVE MATERIAL

This invention relates to the production of a surface active material comprising or consisting of one or more fatty acid esters of sucrose.

Esters of sucrose with fatty acids, particularly the sucrose mono-esters and di-esters, are potentially very valuable as surfactants and have a number of unique advantages in this role. Thus, they are non-toxic, odourless and tasteless; they are non-irritating to the skin; and, when ingested, they hydrolyse to form normal food products. Unlike most surfactants, they are biodegradable under both aerobic and anaerobic conditions; and, unlike most other non-ionic surfactants, they are solid and thus readily usable in powdered or spray-dried products. They are very good emulsifiers; and they perform well as detergents, either along or in combination with anionic surfactants, and can be formulated either as hig-foaming or low-foaming detergents. Accordingly, they can be used generally as domestic or industrial detergents, and also in specialized uses such as additives for foodstuffs, animal feeds, cosmetics, pharmaceuticals and agricultural chemicals. However, in spite of possessing these advantages, sucrose ester surfactants have never been exploited to their full potential, because of difficulties arising in their production. Many processes have been proposed for the preparation of sucrose ester surfactants but, due to technical and economic disadvantages, it is still difficult to achieve large-scale industrial production at a price competitive with other surfactants.

Sucrose esters cannot be prepared by the direct esterification of sucrose with a fatty acid, but three other methods are possible: reaction with a fatty acid chloride; reaction with a fatty acid anhydride; and transesterification with a fatty acid ester. The reaction with acid chlorides, which is performed in the presence of pyridine, is uneconomical and will not give good yields of sucrose mono-esters or di-esters; it can be used to prepare sucrose octa-esters, but these are unsatisfactory as surfactants. Acid anhydrides of the higher fatty acids are not available commercially, and their preparation is complicated and expensive. Consequently, attempts at finding a commercial process for the preparation of sucrose ester surfactants have concentrated on the trans-esterification reaction, generally using methyl or glyceryl esters of fatty acids.

Most of the known trans-esterification processes are carried out in a solvent. The most commonly used solvent is dimethylformamide. The reaction is usually performed at about 90° C, in the presence of an alkaline catalyst (e.g. potassium carbonate), using the methyl ester of the fatty acid. It is necessary to remove all traces of water, by heating the system under reduced pressure as each component is added; and the methanol, or other alkanol, by-product of the trans-esterification must also be removed by prolonged heating of the reaction mixture under reduced pressure, so as to drive the reaction equilibrium in the desired direction. The critical need for anhydrous conditions, the prolonged heating under reduced pressure and, above all, the use of a solvent such as dimethylformamide are all serious disadvantages of this process; not only must the dimethylformamide be recovered for economic operation, but its residual presence can render the product toxic and smelly. It is generally necessary to employ a substantial excess of sucrose in the reaction, and this also has to be removed from the product.

In a modified form of the solvent trans-esterification process, sucrose is reacted with a methyl ester, such as methyl tallowate, in a solvent such as propylene glycol which dissolves the sucrose but not the fatty component. An emulsifying agent is used, and the reaction is performed in a so-called "micro-emulsion". Although this process avoids the disadvantages arising from the use of a toxic solvent such as dimethylformamide, it still employs an expensive solvent which has to be recovered, and it still has to be performed under reduced pressure and in the absence of any water.

A more recent modification of the solvent trans-esterification process, described in British Pat. specification No. 1,332,190, uses water as the solvent. The sucrose is completely dissolved in water, in the presence of a fatty acid soap, a fatty acid ester and a trans-esterification catalyst are added, and the mixture is dehydrated under reduced pressure and at elevated temperature so as to produce a homogeneous melt. The melt is then maintained at elevated temperature, for the trans-esterification reaction to take place. Although this process avoids the problems which arise when using an organic solvent such as dimethylformamide or propylene glycol, it is a multi-stage process which still requires heating under reduced pressure, and the pressure must be carefully controlled in relation to the temperature when producing the dehydrated melt, in order to avoid hydrolysis of the fatty acid ester. The process is, therefore, undesirably complicated for use on an industrial scale.

A solvent-free trans-esterification process has also been proposed recently [vide J. Amer. Oil Chem. Soc. 1970, 47, (2), 56–60; and U.S. Pat. No. 3,714,144]. In accordance with this process, it is stated that the solvent-free trans-esterification must be carried out with the sucrose in the molten state; and the process is, therefore, performed at a temperature of from 170° to 190° C. After a short time, the molten sucrose begins to degrade to a black tarry mass, and the reaction with the fatty acid ester must necessarily be performed very quickly; the reaction is generally stopped within 20 minutes, and sometimes after only 2 minutes. As in the solvent processes, the reaction is performed under reduced pressure, to distil off the alcoholic by-product. Furthermore, the reaction must be performed in the presence of an alkali-free anhydrous soap, which serves to solubilize the fatty acid ester in the molten sucrose and to catalyse the trans-esterification; alkoxides, free alkalis and ordinary soaps are entirely unsatisfactory as catalysts in this process, and their presence results in very rapid decomposition of the sucrose and darkening of the reaction mixture. Thus, although this process avoids some of the disadvantages arising from the use of a solvent such as dimethylformamide, it has disadvantages of its own tending to make it unsatisfactory as a commercial-scale preparation for sucrose ester surfactants. Specifically, it is difficult to control because the reaction must be completed very quickly to avoid degrading the sucrose, it must still be performed under reduced pressure, and it requires the use of expensive special catalysts.

A process which utilises no solvent and keeps the sucrose in the solid phase is described in U.S. Pat. No. 3,558,597. In this process, the trans-esterification of sucrose with a fatty acid alkyl ester is conducted in the presence of a basic trans-esterification catalyst under conditions chosen to distil off the alcohol by-product. These conditions are a temperature of from 100° to 170° C and a pressure of 0.1 to 500 mm Hg, i.e. a pressure considerably below atmospheric pressure and typically about 15 mm Hg. Thus, even in this process low pressure conditions are required.

In British Pat. Specification No. 1,399,053, it has already described how, contrary to all previous proposals, it was surprisingly discovered that sucrose ester surfactants can be prepared by the trans-esterification of sucrose with triglycerides, without using a solvent for any of the reactants, without performing the reaction in molten sucrose, without having to complete the reaction in a short time, without performing the reaction under reduced pressure, and without the use of a special type of catalyst, thus providing a simple and cheap process for the preparation of sucrose ester surfactants which does not require the use of special solvents or reagents or operation under difficult conditions such as a partial vacuum, which overcomes the most serious technical and economic disadvantage of previous processes, and which is consequently eminently suitable for use on an industrial scale. In accordance with the process of said Patent, a surfactant is prepared by reacting solid particulate sucrose with at least one triglyceride in the presence of a basic trans-esterification catalyst, at a temperature in the range of from 110° to 140° C, at atmospheric pressure and in the absence of any solvent.

It has now further been discovered that the process of said Patent can be modified by using one or more fatty acid alkyl esters in place of the triglyceride, in the trans-esterification with sucrose, with the advantage that the yield of especially valuable sucrose mono-ester in the product can be increased thereby.

Accordingly, the invention provides a process for the preparation of a surface active material comprising reaction of solid particulate sucrose with at least one alkyl ester of a fatty acid having 1 to 6 carbon atoms in the alkyl moiety and at least 8 carbon atoms in the fatty acid moiety, in the presence of a basic trans-esterification catalyst, at a temperature from 110° to 140° C, at atmospheric pressure and in the absence of any solvent.

It will be appreciated that the process of the present invention, like that of said Patent, is completely different from the previous ones, in that it uses a heterogeneous reaction mixture wherein the solid particulate sucrose is suspended in the fatty acid ester at atmospheric pressure, whereas the previous processes mostly aimed at achieving a homogeneous system by either dissolving or melting the sucrose, and always utilised a reduced pressure. In view of the methods used in the prior art processes, it is very surprising to find that an effective surfactant material, containing a substantial proportion of the desirable sucrose mono-ester, can be obtained without the use of a solvent and without melting the sucrose, at atmospheric pressure, under the conditions of the present invention.

One or more lower alkyl esters of fatty acids having at least 8 carbon atoms, preferably from 10 to 22 and most preferably from 16 to 18 carbon atoms, may be used in the process of the invention. Preferably, methyl esters are used. It is normally convenient to use lower alkyl esters derived from naturally occurring mixtures of triglycerides, for example, methyl tallowate which contains methyl esters of stearic, palmitic and oleic acids; but lower alkyl esters derived from other triglyceride fats and oils can be used, for example from lard, palm oil, cottonseed oil, soybean oil, olive oil, groundnut oil, coconut oil, castor oil and linseed oil. However, it is generally less desirable to use lower alkyl esters of highly unsaturated fatty acids, for example, derived from the so-called "drying oils" such as linseed oil, because they tend to oxidize and become discoloured during the process of the invention, and the product has relatively inferior surfactant properties; in general, it is preferred to use lower alkyl esters of acids containing not more than one double bond. The presence of hydroxyl groups in the acid chain can also be detrimental to the surfactant properties of the product. Table 1 shows the composition of some examples of triglyceride fats and oils, in terms of the fatty acids from which they are derived and the number of carbon atoms in the acid chains, of which the corresponding lower alkyl esters are suitable for use in the process of the invention. While methyl esters are preferred, ethyl, propyl or butyl esters may, for example, also be used.

The lower alkyl ester and sucrose are suitably used in substantially equimolar amounts, although the proportions are not critical. In the case of an alkyl tallowate, such as methyl tallowate, for example, the amount can be calculated on the basis of the alkyl stearate.

Table I

| | | | | | | | | | | | | | | | | | |
|---|---|---|---|---|---|---|---|---|---|---|---|---|---|---|---|---|---|
| | | | | | | Composition of natural triglycerides (% by weight) | | | | | | | | | | | |
| Triglyceride fat or oil | Caprylic C8 | Capric C10 | Lauric C12 | Myristic C14 | Myristoleic C14 | Pentadecanoic C15 | Palmitic C16 | Palmitoleic C16 | Margaric C17 | Stearic C18 | Oleic C18 | Linoleic C18 | Linolenic C18 | Ricinoleic C18 | Arachdic C20 | Eicosenoic C20 | Behenic C22 |
| Tallow | | | | 3.2 | 1.0 | 0.4 | 26.4 | 2.6 | 0.9 | 26.9 | 36.7 | (~1) | | | | | |
| Linseed | | | | | | | 6.3 | | | 4.3 | 18.2 | 14.3 | 56.7 | | | | |
| Cottonseed | | | | 0.6 | | | 21.7 | | | 2.1 | 17.8 | 57.9 | | | | | |
| Palm | | | | 0.9 | | | 46.6 | | | 4.1 | 39.3 | 9.1 | | | | | |
| Soybean | | | | | | | 10.5 | | | 3.8 | 23.7 | 55.5 | 6.6 | | | | |
| Groundnut | | | | | | | 9.0 | | | 3.5 | 64.5 | 18.2 | | | 1.2 | (0.9?) | (1.6?) |
| Coconut | 8.0 | 6.7 | 51.3 | 16.2 | | | 7.6 | | | 2.7 | 5.9 | 1.6 | | | | | |
| Castor | | | | | | | 0.9 | | | | 9.6 | 10.3 | | 79.0 | | | |

The catalyst used in the process of the invention may be any of the basic compounds conventionally used as trans-esterification catalysts, but alkali metal carbonates and alkoxides, e.g. potassium carbonate and sodium methoxide, are found to give particularly good results. Other basic compounds, such as tertiary or quaternary organic bases, silicates and borates may also be used. If desired, a mixture of such compounds may be employed. The catalyst concentration is not critical, but it is generally desirable to use at least 2% of catalyst in order to attain a satisfactory rate of reaction and thus produce a surfactant material within a reasonably short time. The reaction can be accelerated by using higher concentrations of 5 to 12%, preferably about 10%. In general, no additional benefit is derived by further raising the catalyst concentration, and levels of above 20% are not likely to be used in practice. (All these percentage concentrations are by weight, on the basis of the weight of the reaction mixture).

In carrying out the process of the invention, the sucrose and the basic catalyst can be added to the alkyl ester and the resulting suspension heated with stirring, to bring about the trans-esterification reaction. Alternatively, the alkyl ester can first be heated with the catalyst alone, so that it is partly saponified, and the sucrose then added to the reaction mixture for the trans-esterification to take place. However, this preliminary saponification step is generally unnecessary when using a surfactant, in accordance with the preferred embodiment of the invention described hereinafter.

Although no solvent is used in the process of the invention, the reaction is performed at a temperature well below the melting point of sucrose, in the range of from 110° to 140° C. The preferred temperature range is from 120° to 130° C, and the reaction is most preferably performed at about 125° C. (All these values refer to the internal temperature of the reaction mixture). Substantially no reaction takes place at temperatures below 110° C, while at temperatures above 140° C charring occurs and the product does not have satisfactory surfactant properties. The reaction mixture can be maintained at the desired temperature by any conventional means allowing adequate heat transfer and temperature control, for example, by providing the reaction vessel with an external jacket through which steam is passed. In some cases, especially if violent agitation is applied to the reaction mixture, it may be necessary to cool the mixture during the course of the reaction so as to maintain the required temperature, for example, by passing water through the external jacket. The process is carried out at atmospheric pressure; for example, it can be carried out in a simple open reaction vessel provided with suitable heating and stirring means. A conventional type of motor-driven stirrer may be used; but in order to provide adequate mixing and keep the temperature constant throughout the reaction mixture, especially in a large vessel, it is sometimes desirable to use a high-shear mixer driven at several thousand revolutions per minute.

No special conditions are chosen to distil off the alcohol by-product. When the alcohol by-product is particularly low-boiling, for example methanol (b.p. 65° C) and ethanol (b.p. 78° C), some may distil out under the reaction conditions. The extremely viscous nature of the reaction mixture does, however, prevent free distillation and in order to remove substantially all the alcohol it has been considered necessary in the prior art processes, to use considerably reduced pressure. Thus the use of atmospheric pressure might be thought to result in a significant proportion of the alcohol by-product remaining in situ. Surprisingly, however, the yield of sucrose ester, especially the mono ester, is not reduced and may actually be increased.

We have found that a surprising advantage of using atmospheric pressure, apart from the simpler apparatus involved, is the fact that the sucrose is very much more easily maintained in suspension in the ester. At reduced pressures phase separation occurs and, since the reaction can only occur at the interface, the rate of reaction is decreased. At atmospheric pressure, however, the sucrose can be kept in finely distributed suspension in the reaction mixture and the rate of reaction and the yield are enhanced even if the alcohol by-product is not completely removed.

The sucrose used in the process of the invention is normally in the form of particulate refined sugar, such as granulated sugar. The sucrose particle size is not critical, but particles which are too large can be difficult to disperse adequately in the reaction mixture, and it is therefore generally preferred to use sucrose of a particle size smaller than 250 microns. The sucrose can be ground and sieved before use, so as to obtain the desired particle size, but this is unnecessary if a high-shear mixer is being used to agitate the reaction mixture, since such a mixer will immediately comminute the sucrose particles.

Unlike the trans-esterification processes using an organic solvent, the process of the present invention does not require dehydration of the reactants, and the traces of water normally present in the starting materials are not detrimental. On the other hand, the process of the invention does not use water as a reaction solvent, and its presence at levels in excess of about 1% by weight tends to be detrimental, because the reaction slows down, the sucrose tends to form large lumps, and soap formation rapidly occurs.

The duration of the reaction depends upon the nature of the alkyl ester, the amount and type of catalyst, the efficiency of mixing, and the reaction temperature used. The mixture becomes more viscous as the reaction proceeds, and the reaction is terminated when the mixture becomes too viscous for adequate stirring. The reaction can be finished in as little as 6 hours, but is sometimes continued for 14 to 16 hours, or even longer, in order to obtain optimum yields of surfactant. The progress of the reaction can be followed, for example, by subjecting samples of the reaction mixture to chromatography at appropriate time intervals.

It is highly preferred to perform the process of the invention in the presence of a surfactant. The most effective surfactant so far discovered is the surfactant product of the present process or of the corresponding process starting from the triglyceride, and this is suitably added at a concentration of 5 to 10% by weight, based on the total weight of the reaction mixture. Other effective surfactants, which may be added in similar quantities, are diglycerides and monoglycerides, the former being more effective than the latter. Soaps such as sodium stearate are found to be less effective for this purpose. It is theorized that these additives act as physical catalysts in the heterogeneous solid/liquid reaction system used in the process of the invention. The use of a surfactant in this way is particularly advantageous when the basic trans-esterification catalyst is used in low concentrations. If a small proportion of the surfactant product, or of a diglyceride or monoglyceride, is added to the reaction mixture, the reaction time is considerably shortened.

The product of the process contains the sucrose mono-ester of the fatty acid together with various unreacted starting materials and by-products. This product has notable surfactant properties and can be used in an unrefined state as a biodegradable, non-toxic surfactant for many cleansing purposes. A large proportion of the product is made up of the sucrose mono-esters which are particularly valuable as surfactants, this proportion generally being higher than in a product of the corresponding process starting from triglycerides instead of lower alkyl esters. The product of the reaction solidifies when it cools and it can then be formulated into various compositions; for example, it can be formulated with the conventional extenders and adjuvants, to produce detergent powder compositions. Compositions for other purposes, such as cosmetics, foodstuffs and agricultural chemicals, can be formulated in the conventional manner. Since no solvent is used in the process of the invention, the costly and complicated steps of solvent recovery and product purification are completely avoided.

There is a need however for the preparation of relatively pure mono-esters for use as surfactants, emulsifiers etc. in such fields as foodstuffs, fine toiletries, pharmaceuticals, rubber and plastics, paints and brewing.

Various purification techniques have been proposed for sucrose mono-esters, depending on the reaction medium used to prepare them. These techniques have largely relied on partition between solvents, a technique which is complicated by the efficiency of the desired product as an emulsifier.

We have now found that the trans-esterification process can be followed by a simple three-stage purification procedure to yield a sucrose mono-ester product of at least 80% purity.

According to a further feature of the present invention, therefore, there is provided a process for preparing a surfactant which comprises reacting solid particulate sucrose as defined above; and then (a) treating the crude reaction product with an aqueous salt of a metal capable of forming an insoluble salt (soap) with a fatty acid, and separating the insoluble material; (b) extracting the separated insoluble material with an organic solvent in which lower alkyl esters of fatty acids are soluble but sucrose mono- and di-esters are substantially insoluble; and (c) extracting the insoluble residue from (b) with a polar solvent for sucrose mono- and di-esters, but in which fatty acid soaps are substantially insoluble.

The treatment in stage (a) is conveniently with a Group 2 metal salt and serves to convert any free fatty acid and/or soaps thereof into water-insoluble Group 2 metal soaps. The aqueous salt solution must thus contain sufficient Group 2 metal salts for complete conversion. Typical Group 2 metals include calcium, magnesium and barium in Group 2a and zinc in Group 2b, calcium being particularly preferred.

The solid residue from stage (a) can be filtered off, conveniently on a rotary drum filter. The separation of the insoluble residue is improved if the slurry obtained in step (a) is gently stirred at a moderately elevated temperature (e.g. about 35° C). This treatment helps to coagulate the solid material so that it can be more easily filtered.

The cake obtained from the filtration is then submitted to stage (b) of the purification, namely, solvent extraction, preferably after being dried. Any convenient solvent may be used which is a good solvent for lower alkyl esters of fatty acids and sucrose higher esters (i.e. sucrose esterified with more than two fatty acid moieties). Ketonic solvents such as acetone and methyl ethyl ketone are suitable in this extraction, but more preferably a less polar water-immiscible solvent is used, for example, an ester such as ethyl acetate. This extraction removes fatty acid lower alkyl esters, where present in the reaction mixture, and also the higher esters of sucrose. Any of these esters can be recovered as by-products from the solvent extract.

The residue from this extraction contains mainly the desired sucrose mono-ester and di-ester and the Group 2 metal soaps, together with a small quantity of sucrose. Extraction of this residue in stage (c) is preferably effected using a lower alcohol containing 1 to 4 carbon atoms. The extraction eliminates the soaps as an insoluble residue and provides an alcoholic extract containing a purified material comprising at least 80% of the desired sucrose mono-ester. Any convenient lower alcohol can be used, but it is preferred to use ethanol or isopropanol. Removal of the alcohol from the obtained extract yields a purified product.

The invention is illustrated by the following Examples.

EXAMPLE 1

A mixture of 40 g of methyl tallowate, 17 g of sucrose, 5 g of potassium carbonate and 2.5 g of surfactant (prepared from sucrose and tallow by the process of said U.S. Pat. No. 1,399,053) was stirred for 11 hours at 125° C. The thick, waxy material produced hardened to a brittle solid on cooling. Yield 48 g. The product had good surfactant properties and contained approximately 30% by weight of sucrose mono-esters, with some di-esters and higher esters.

EXAMPLES 2 – 15

Similar reactions were effected with the reactants and results detailed below.

| | Me oleate (g) | Sucrose (g) | $K_2CO_3$ (g) | Emulsifier (g) | Total wt (g) | yield (g) | loss of wt. (g) | temp ° C | reac$^n$ time | reac$^n$ % | sucrose monoester % | sucrose % | K soaps % | Me esters % | higher esters % |
|---|---|---|---|---|---|---|---|---|---|---|---|---|---|---|---|
| 2) | 80 0.28m 64.5% | 34 0.1 27.4% | 10 8.1% | — | 124 | 108 110 | 16 14 | 125° 125° | 16h 23 | 31.2 27.6 | 11.6 7.2 | 17.1 17.0 | 14.1 20.3 | 26 21.4* |
| 3) | 80 | 34 | 10 | 6.2 5% on 124g | 1) 130.2 2) | 114 117.7 | 16.2 13.7 | 125° 125° | 16h 18h | 28.7 36.3 | 12.1 9.5 | 12.7 19.5 | 18.9 13.3 | 27.6 21.4 |
| 4) | 53.4 0.189m 54.8% | 34 0.1m 34.9% | 10 10.3% | | 97.4 | 84 | 13.4 | 125° | 12h | 28.9 | 8.8 | 21.1 | 9.7 | 31.5 |
| 5) | 53.4 | 34 | 10 | 4.87 5% on 97.4g | 1) 102.17 2) | 95.3 96 | 7.1 6.4 | 125° 125 | 16h 16h | 18.1 24.3 | 22.4 18.3 | 11.0 11.8 | 16.7 13.6 | 31.8 32 |
| 6) | 26.7 0.095m 37.8% | 34 48.1 | 10 14.1 | | 1) 70.7 2) 70.7 | 60.5 61.5 | 10.2 9.2 | 125° | 10h 8h | 15.1 12 | 43 71.8 | 8.3 5.0 | 5.5 11.8 | 28.1* —* |
| 7) | 26.7 | 34 | 10 | 3.5 | 1) 74.2 | 67.5 | 6.7 | 125° | 10h | 28 | 32.3 | 12.7 | 1.3 | 25.7 |

-continued

| | | 5% on 70.7 | 2) 74.2 | | 67.3 | 6.9 | 125° | 8h | 33.8 | 42.1 | 14.7 | 2.8 | 26.6 |
|---|---|---|---|---|---|---|---|---|---|---|---|---|---|
| Me oleate | Sucrose | $K_2CO_3$ | Emulsifier | Total wt. | Yield (g) | Loss of wt. | Temp. | reac. time | Sucrose monoester | Sucrose | K soaps | Me esters | Higher esters |
| 8) 53.4 0.189m 56.7% | 34 0.1m 36.2% | 6.7 7.1% | | 94.1 | 1) 75 | 19.1 | 125° | 20h | 37.7 | 8.2 | 15 | 8.0 | 31.1* |
| 9) 53.4 | 34 | 6.7 | 4.7 | 98.8 | 1) 87 2) 85 | 11.8 13.7 | 125 125 | 20h 22h | 31.1 31.4 | 24.2 17.2 | 13.2 6.7 | 13.2 0.3 | 17.8 |
| 10) 26.7 0.095m 39.6% | 34 0.1m 50.4% | 6.7 10% | 3.37 | 70.77 | 1) 65 2) 65 3) 64 4) 64.5 | 4.23 4.23 5.23 4.83 | 125 125 125 125 | 9h 9h 8h 9H | 22.8 40.0 24.1 36.5 | 46.3 43.7 48.5 36.8 | 9.4 13.1 9.4 14.8 | 8.0 3.2 3.2 0.6 | 14.5 — 10.8 11.3 |
| 53.4 | 34 | 3.85 4.2% | 4.7 | 95.95 | 1) 74 2) 83 3) 85 4) 85.5 | 22 13 11 10.5 | 125 125 125 125 | 24h 24h 24h 24h | 19.9 30.3 18.3 34.8 | 30.7 21.8 21.5 17.2 | 9.0 11.9 8.9 14.9 | 20.7 8.3 21.0 1) 64 | 20.7* 27.7 31.3 5.9 |
| 12) 26.7 | 34 | 3.55 | 3.55 | 67.42 | 1) 64 2) 60 | 3.42 7.42 | 125 125 | 12h 12h | 28.8 13.2 | 41.8 50.9 | 13.3 1.7 | 6.5 23.6 | 9.6 0.6 |

| | | | | Reaction of methyl ester with sucrose using potassium carbonate catalyst | | | | | | | | | |
|---|---|---|---|---|---|---|---|---|---|---|---|---|---|
| Me ester | Sucrose | $K_2CO_3$ | Emulsifier | Total wt | yield (g) | loss of wt | temp | react<sup>n</sup> time | sucrose monoester | sucrose | K soaps | Me esters | higher esters |
| 13) Me tallowate 80g 64.5% | 34 27.4% | 10g 8.1% | 5.0 | 129g | 1) 96g 2) | 33 | 125 125 | 11h 14h | 27.0 32.0 | | | | |
| 14) Me tallowate 53.4 54.8% | 34 34.9% | 10 10.3% | 5.0 | 102.4g | 88g | 14.4 | 125 | 7h | 20.2 | | | | |
| 15) Me tallowate 26.6 37.8% | 34 48.1% | 10 14.1% | 5.0 | 75 6g | 66g | 9.6 | 125 | 9h | 36.6 | | | | |

*Indicates sucrose had formed lumps in the reaction media

I claim:

1. A process for the preparation of a surface active material comprising reacting solid particulate sucrose with at least one alkyl ester of a fatty acid having 1 to 6 carbon atoms in the alkyl moiety and at least 8 carbon atoms in the fatty acid moiety, in the presence of a basic trans-esterification catalyst, at a temperature from 110° to 140° C, at atmospheric pressure without intentionally distilling alcohol by-product and in the absence of any solvent.

2. A process according to claim 1 in which the fatty acid ester has a fatty acid moiety with 10 to 22 carbon atoms.

3. A process according to claim 1 in which the fatty acid ester has a fatty acid moiety with 16 to 18 carbon atoms, in which the catalyst is used at a concentration of 5 to 12%, in which the temperature is about 125° C., and in which the sucrose is of a particle size less than 250 microns.

4. A process according to claim 1 in which the alkyl fatty acid ester is a mixed ester derived from a naturally occurring mixture of triglycerides.

5. A process according to claim 1 in which the alkyl moiety of the ester is a methyl group.

6. A process according to claim 1 in which the basic catalyst is selected from the group consisting of alkali metal carbonates and alkoxides and is present as at least 2% of the reaction mixture.

7. A process according to claim 6 effected at a temperature of 120° to 130° C.

8. A process according to claim 1 effected with high-shear mixing.

9. A process according to claim 1 effected in the presence of a surfactant selected from the group consisting of (a) a previously prepared product of the process or the same process using a triglyceride in place of the alkyl ester; (b) a diglyceride; and (c) a monoglyceride.

10. A process according to claim 9 in which the surfactant is present at a concentration of 5 to 10% by weight.

11. A process for the purification of the reaction product obtained after reacting solid particulate sucrose with at least one alkyl ester of a fatty acid having 1 to 6 carbon atoms in the alkyl moiety and at least 8 carbon atoms in the fatty acid moiety, in the presence of a basic trans-esterification catalyst, at a temperature from 110° to 140° C, at atmospheric pressure, without intentionally distilling alcohol by-product and in the absence of any solvent, comprising (a) treating the crude reaction product with an aqueous salt of a metal capable of forming an insoluble salt (soap) with a fatty acid, and separating the insoluble material; (b) extracting the separated insoluble material with an organic solvent in which lower alkyl esters of fatty acids are soluble but sucrose mono- and di-esters are substantially insoluble; and (c) extracting the insoluble residue from (b) with a polar solvent for sucrose mono- and di-esters, but in which fatty acid soaps are substantially insoluble.

12. A process according to claim 11 in which the aqueous salt used is a salt of a Group 2 metal and in which the solvent in step (b) is a ketone or an ester and the solvent in step (c) is a lower alcohol with 1 to 4 carbon atoms.

13. A process according to claim 12 in which the salt is a calcium salt.

14. A process according to claim 11 in which the slurry obtained in step (a) is gently stirred at a moderately elevated temperature before separation.

15. A process according to claim 12 in which the solvent in step (b) is selected from the group consisting of acetone, methyl ethyl ketone and ethyl acetate and in step (c) is selected from the group consisting of ethanol and isopropanol.

16. A process for the preparation of a surface active material comprising reacting solid particulate sucrose with at least one alkyl ester of a fatty acid having 1 to 6 carbon atoms in the alkyl moiety and 16 to 18 carbon atoms in the fatty acid moiety, in the presence of a basic trans-esterification catalyst at a temperature of about 120° to about 130° C at atmospheric pressure, without intentionally distilling alcohol by-product and in the absence of any solvent; the reaction being effected in the presence of a surfactant selected from (a) a previously prepared product of the process or of the same process using a triglyceride instead of the alkyl ester; (b) a diglyceride; or (c) a monoglyceride; and then purifying the reaction product by (a) treating the crude reaction product with an aqueous salt of a Group 2 metal selected from the group consisting of calcium, magnesium, barium and zinc and separating the insoluble material from the slurry so formed; (b) extracting the separated insoluble material with an organic solvent selected from the group consisting of ketone and ester solvents to remove lower alkyl esters of fatty acids and leave an insoluble residue; and (c) extracting the insoluble residue from step (b) with a polar solvent selected from the group consisting of lower alcohols with 1 to 4 carbon atoms and evaporating the extract to dryness.

* * * * *